(12) United States Patent
Caswell et al.

(10) Patent No.: US 8,129,430 B2
(45) Date of Patent: Mar. 6, 2012

(54) METHOD OF REDUCING PHOSPHATE NEPHROPATHY IN A MAMMAL

(75) Inventors: Michael L. Caswell, Lynchburg, VA (US); Gilbert W. Moeckel, Guilford, CT (US)

(73) Assignee: C.B. Fleet Company, Inc., Lynchburg, VA (US)

( * ) Notice: Subject to any disclaimer, the term of this patent is extended or adjusted under 35 U.S.C. 154(b) by 387 days.

(21) Appl. No.: 12/195,853

(22) Filed: Aug. 21, 2008

(65) Prior Publication Data

US 2009/0062387 A1 Mar. 5, 2009

Related U.S. Application Data

(60) Provisional application No. 60/969,293, filed on Aug. 31, 2007.

(51) Int. Cl.
*A61K 31/194* (2006.01)

(52) U.S. Cl. ..................................................... 514/574

(58) Field of Classification Search .................. None
See application file for complete search history.

(56) References Cited

U.S. PATENT DOCUMENTS

| | | | |
|---|---|---|---|
| 2004/0071779 A1 | 4/2004 | Keiser et al. | |
| 2004/0192614 A1 | 9/2004 | Vanner et al. | |
| 2006/0051428 A1 | 3/2006 | Ayala et al. | |

FOREIGN PATENT DOCUMENTS

| | | |
|---|---|---|
| WO | WO 88/03762 | 6/1988 |
| WO | WO 98/26776 | 6/1998 |
| WO | WO 2006/028632 | 3/2006 |
| WO | WO 2007/022435 | 2/2007 |

OTHER PUBLICATIONS

Abueb, J.G., New England Journal of Medicine, (2007), 357, pp. 797-805.*
International Search Report dated Dec. 4, 2008 for PCT Application No. PCT/US08/073855.
Gimenez, L., et al., "Prevention of phosphate-induced progression of uremia in rats by 3-phosphocitric acid", Kidney International, vol. 22, pp. 36-41, (1982).
Zechner, V. O., et al., "The Conservative treatment of phosphate calculi with citrate buffer", Wiener Klinische Wochenschrift, vol. 87, No. 9, pp. 300-303, (1975).
Desmeules, S. et al., "Acute Phosphate Nephropathy and Renal Failure," NEJM, 349, pp. 1006-1007, (2003).
Orias, M. et al., "Extreme Hyperphosphatemia and Acute Renal Failure after a Phosphorus-Containing Bowel Regimen," Am J Nephrol, 19, pp. 60-63, (1999).
Markowitz, G.S. et al., "Renal Failure Due to Acute Nephrocalcinosis Following Oral Sodium Phosphate Bowel Cleansing," Human Pathology, 35, 675-684, (2004).
Markowitz, G.S. et al., "Acute Phosphate Nephropathy following Oral Sodium Phosphate Bowel Purgative: An Underrecognized Cause of Chronic Renal Failure," J Am Soc Nephrol, 16, pp. 3389-3396, (2005).
Fine, A. et al., "Severe Hyperphosphatemia Following Phosphate Administration for Bowel Preparation in Patients With Renal Failure: Two Cases and a Review of the Literature," American Journal of Kidney Diseases, vol. 29, No. 1, pp. 103-105, (1997).
Ritskes-Hoitinga, J. et al., "Phosphorus-Induced Nephrocalcinosis and Kidney Function in Female Rats," J. Nutr., 119, pp. 1423-1431, (1989).
Rao, G.N., "Diet and Kidney Diseases in Rats", Toxicologic Pathology, vol. 30, No. 6, pp. 651-656, (2002).
Oikawa, T. et al., "Modulation of plasminogen activator inhibitor-1 in vivo : A new mechanism for the anti-fibrotic effect of rennin-angiotensin inhibition," Kidney International, vol. 51, pp. 164-172, (1997).
Ma, L-J et al., "Model of robust induction of glomerulosclerosis in mice: Importance of genetic background," Kidney International, vol. 64, pp. 350-355, (2003).
Moeckel, G.W. et al, "Distribution of de novo synthesized betaine in rat kidney: role of renal synthesis on medullary betaine accumulation," Am. J. Physiol., 272, pp. F94-F99, (1997).
Moeckel, G.W. et al, "COX2 Activity Promotes Organic Osmolyte Accumulation and Adaptation of Renal Medullary Interstitial Cells to Hypertonic Stress," Journal of Biological Chemistry, vol. 278, No. 21, pp. 19352-19357, (2003).
Smoyer W.E., et al., "Ischemic Acute Renal Failure Induces Differential Expression of Small Heat Shock Proteins," J Am Soc Nephrol, 11, pp. 211-221, (2000).
Neuhofer, W. et al., "Chronic COX-2 inhibition reduces medullary HSP70 expression and induces papillary apoptosis in dehydrated rats," Kidney International, vol. 65, pp. 431-441, (2004).
Moeckel, G. W. et al., "Role of integrin $\alpha_1\beta_1$ in the regulation of renal medullary osmolyte concentration," Am J Physiol Renal Physiol, 290, pp. F223-F231, (2006).
Marangella, M. et al., "Crystallization Inhibitors in the Pathophysiology and Treatment of Nephrolithiasis," Urologia Int., 72, Suppl. 1, pp. 6-10, (2004).
Toblli, J.E. et al., "Potassium citrate administration ameliorates tubulointerstitial lesions in rats with uric acid nephropathy," Clinical Nephrology, vol. 55, No. 1, pp. 59-68, (2001).
Lacour, B. et al., "Effet du citrate et des phosphate sur le transport du calcium dans l'iléon de rat in vitro," Gastroenterol Clin. Biol., 18, pp. 938-944, (1994). (Summary in English).
Vanner, S.J. et al., "A Randomized Prospective Trial Comparing Oral Sodium Phosphate with Standard Polyethylene Glycol-Based Lavage Solution (Golytely) in the Preparation of Patients for Colonoscopy," The American Journal of Gastroenterology, vol. 85, No. 4, pp. 422-427, (1990).

* cited by examiner

*Primary Examiner* — Phyllis G. Spivack
(74) *Attorney, Agent, or Firm* — Evan Law Group LLC (57) ABSTRACT

The present invention provides the invention provides methods of reducing phosphate nephropathy in a mammal suffering from impairment of renal function, including administering to the mammal an amount of citrate that is effective to reduce serum phosphorous concentration.

8 Claims, 7 Drawing Sheets

METHOD OF REDUCING PHOSPHATE NEPHROPATHY IN A MAMMAL

CROSS REFERENCE TO RELATED APPLICATION

This application claims priority to provisional application No. 60/969,293 entitled "METHOD OF PREVENTING NEPHROCALCINOSIS" filed 31 Aug. 2007, the entire contents of which are hereby incorporated by reference, except where inconsistent with the present application.

BACKGROUND

Prior to colonoscopy, including virtual colonoscopy procedures, the colon must be cleansed so the surgeon may see any polyps and other lesions that are located on the interior surface of the colon. Additional cleansing procedures of the colon are carried out prior to radiological tests or surgical interventions. This cleansing generally entails the drinking of one or more cathartic solutions. Aqueous solutions of sodium phosphate salts (monobasic and dibasic sodium phosphate), such as FLEET® PHOSPHO-SODA®, are very effective oral cathartics and are extensively used prior to the above mentioned procedures. For pre-colonoscopy use, a split regimen is often preferred that includes one 45 mL dose given the evening before colonoscopy and a second 30 mL dose given at least three hours prior to the procedure on the following morning.

Ingestion of phosphate-rich medicaments, for example oral sodium phosphates solutions for bowel cleansing prior to a colonoscopy, has been found to induce significant increases in serum phosphorous concentration (18, 19). While normal ranges of serum phosphorous concentration fall between 2.5 and 4.1 mg/dl, patients given oral sodium phosphates solutions exhibit increases in serum phosphorous to an average of 7.2±0.6 mg/dl (18). These increases in serum phosphorous concentration were not affected by the administration of oral rehydration solution (ORS) (19).

Calcium phosphate crystal formation and concomitant decline in kidney function has been shown to be augmented in patients suffering from diseases which affect renal blood flow and glomerular filtration rate, such as ischemia-induced renal failure (5). Moreover, high phosphate diet has been shown to induce calcium phosphate crystal deposition in kidneys of normal rats, without impairment of renal function (6, 7). It was also shown that male Sprague-Dawley rats on high phosphate diet deposit calcium phosphate crystals in kidney tubules after being intermittently dehydrated. Furthermore, previous studies have suggested a predisposition of female rats to calcium phosphate crystal deposition following high phosphate diet.

Phosphate nephropathy consists of damage to kidneys caused by formation of calcium phosphate crystals or direct toxicity to cells within the renal tubules. The result is damage to the nephron, which can cause acute renal insufficiency or acute renal failure. A kidney biopsy in the setting of phosphate nephropathy typically shows the pathological findings of diffuse tubular injury with calcium phosphate crystal deposition.

SUMMARY

In a first aspect, the invention provides methods of reducing phosphate nephropathy in a mammal suffering from impaired renal function. The invention includes administering to the mammal an amount of citrate that is effective to reduce serum phosphorous concentration.

In a second aspect, the invention provides methods for reducing kidney damage in a mammal consuming a high phosphate diet, including administration of an amount of citrate to the mammal that is effective to reduce serum phosphorous concentration levels.

In a third aspect, the invention provides methods for reducing kidney injury in a mammal from a high phosphate medicament, including administration of a high phosphate medicament to the mammal and administering an amount of citrate that is effective to reduce the increase in serum phosphorous levels, occasioned by the high phosphate medicament, wherein the citrate is administered from 24 hours prior to and up to 24 hours after, the administration of the medicament.

In a fourth aspect, the invention provides high phosphate medicaments including phosphate and citrate.

BRIEF DESCRIPTION OF THE DRAWINGS

The invention can be better understood with reference to the following drawings and description.

DETAILED DESCRIPTION

The present invention takes advantage of the discovery that citrate protects against phosphate nephropathy, thus preventing injury to the cells of the kidney. Without being bound to any particular theory, it is believed that citrate has a renal protective effect that may be due to complex formation with calcium phosphate.

The above discovery is the result of a study aimed at investigating the effect of citrate on renal function, acute tubular necrosis (ATN) and phosphate crystal formation in male and female Sprague-Dawley rats on a high phosphate diet. It was found that citrate significantly reduced serum phosphorous levels and improved renal function in rats with ischemia/reperfusion (I/R) injury on a high phosphate diet. The morphologic changes in kidney sections correlated with changes in renal function. Rats with increased blood urea nitrogen (BUN) had significant pathologic histology findings showing tubular dilation, epithelial flattening with regenerative changes and sloughing of tubular epithelial cells, consistent with ATN. Moreover, there were multiple large casts, most likely Tamm-Horsfall casts, in injured tubules. Citrate markedly decreased both the extent and severity of injured nephrons and improved renal functional parameters. This leads to the conclusion that phosphate may be directly toxic to tubular epithelial cells, which is independent of calcium-phosphate crystal formation.

Furthermore, the degree of ATN following I/R injury, dehydration and high phosphate diet was not significantly altered by the gender of the animals. Also, citrate treated animals unexpectedly showed decreased BUN levels, but did not show significantly changed serum or urine pH values. Without being bound to any particular theory, it appears that citrate decreases the amount of phosphate reaching the nephron, which decreases phosphate-mediated cell injury. This explains the beneficial effect of citrate on the tubular injury associated with high phosphate diets.

Accordingly, the present invention provides methods for preventing, mitigating or reducing injury to kidneys of mammals suffering from impairment of renal function, for instance mammals with diseases that affect renal blood flow or glomerular filtration rate, such as ischemia-induced renal failure or other types of tubular injury. Also provided are methods for preventing, mitigating or reducing calcium phosphate crystal deposition in kidneys of mammals on high phosphate diet, with or without impairment of renal function.

In addition, the invention provides methods for preventing, mitigating or reducing cell injury in the kidneys of a mammal to which has been administered a high phosphate medicament. This is achieved by administrating citrate to the mammal, preferably from 24 hours prior to the administration of the medicament and up to 24 hours after the administration of the medicament. More preferably, the citrate is administered as a single dose from 1 hour prior to the administration of the medicament to 1 hour after the administration of the medicament. Citrate is preferably administered as citric acid, citrate salts such as sodium citrate ($C_6H_5O_7Na_3$), sodium hydrogen citrate ($HC_6H_5O_7Na_2$) and sodium dihydrogen citrate ($H_2C_6H_5O_7Na_3$), and citrate esters such as ethyl citrate, diethyl citrate and triethyl citrate. The quantity of administered citrate is preferably 0.019 to 0.39 moles of citric acid, citrate salts or esters, for example the number of moles that are contained in 5 g to 100 g of sodium citrate. More preferably the quantity of administered citrate is 0.039 to 0.19 moles of citric acid, citrate salts or esters, for example the number of moles that are contained in 10 g to 50 g of sodium citrate. All weight amounts of citrate as referred to herein are sodium citrate equivalents. For example "20 g of citrate" means a number of moles of citrate as contained in 20 g of sodium citrate.

Representative mammals include humans, laboratory animals such as mice, rats and monkeys, pets such as cats and dogs and other animals such as bovines, sheep, equines and pigs.

Citrate can be administered orally as liquid compositions or as solid unit dosages such as pills, tablets, capsules and powders. Citrate may be administered by adding or mixing it first with a food or a beverage. It may also be administered intravenously or intraperitoneally, as a single or multiple injections, for instance as an intravenous solution administered in the treatment of ischemic injury to the kidney or during dialysis care. The citrate can also be added to the solutions routinely used in dialysis such as Delflex® (Fresenius Medical Care North America Waltham, Mass., USA) or administered in conjunctions with medications that are high in phosphate content, such as oralسodium phosphates solutions, which are phosphate salt cathartics, for example PHOSPHO-SODA® and EZ-PREP® (C. B. Fleet, Lynchburg, Va., USA). Other medications that are high in phosphate content include solid formulations such as Visicol® and OsmoPrep® (Salix Pharmaceuticals, Morrisville, N.C., USA). Citrate may be provided pre-mixed with a high phosphate content medicament, or as kit with the citrate packaged separately from the phosphate. The term "high phosphate medicament" includes any medicament that causes an increase in serum phosphorous concentration such as medicaments which contain phosphate, for example oral sodium phosphate solutions.

Phosphate salt cathartics, such as commercially available FLEET® PHOSPHO-SODA® (C. B. Fleet, Lynchburg, Va.; National Formulary Monograph USP 23/NF18, p. 1430), include monobasic sodium phosphate (sodium dihydrogen phosphate, monohydrate) ($NaH_2PO_4.H_2O$) and dibasic sodium phosphate (disodium hydrogen phosphate, heptahydrate) ($Na_2HPO_4.7H_2O$) in water. In one aspect, the phosphate salt cathartic includes from 0.05 to 1.5 gram/mL of monobasic sodium phosphate and from 0.02 to 0.6 gram/mL of dibasic sodium phosphate. Phosphate salt cathartics have a pH from about 4.4 to about 5.2 and may be produced in multiple ways, such as by combining phosphoric acid with dibasic sodium phosphate or with caustic soda. Cathartics of this type are very stable, thus having a long shelf-life, and are considered to work in a mild and very effective manner.

In another aspect, the phosphate salt cathartic includes from 0.25 to 1 or from 0.4 to 1 gram/mL of monobasic sodium phosphate and from 0.1 to 0.4 or from 0.13 to 0.25 gram/mL of dibasic sodium phosphate. At present, an especially preferred phosphate salt cathartic includes about 0.48 g/mL of monobasic sodium phosphate and about 0.18 g/mL of dibasic sodium phosphate. Phosphate salt cathartics that include one phosphate salt, such as dibasic sodium phosphate, also may be used.

In addition to a water solution, the phosphate salt cathartic may be incorporated into a gel. For example, an aqueous solution containing the phosphate salts may be combined with a gelling agent to form a gel. Suitable gelling agents may include gelatin, such as Gelatin, Type A, 25 Bloom, 50 mesh, from Great Lakes Gelatin, PO Box 917, Grayslake, Ill.; agar, such as Sigma brand Agar A-7002 Lot 71K0093; commercially available products that includes flavorings, such a JELL-O® brand desert mix, and the like. In one aspect, about 85 grams of JELL-O® may be boiled in about 130 mL of water and combined with a near-boiling solution containing 45 mL of FLEET® PHOSPHO-SODA® diluted with about 65 mL of water and the flavorant. Additional details regarding the incorporation of a phosphate salt cathartic into a gel may be found in U.S. Patent Application Publication, Pub. No. US2004-0071779 A1. Prior to consumption, a flavorant may be added to the phosphate salt cathartic to increase its palatability. Further details about flavorants may be found in U.S. Patent Application Publication, Pub. No. US 2006-0051428.

By orally administering the phosphate salt cathartic to a subject, the colon may be cleansed. Generally, the compositions are administered so that from 0.4 to 0.85 grams of monobasic sodium phosphate and from 0.1 to 0.5 grams of dibasic sodium phosphate per kilogram of body weight are consumed. A first aliquot of the composition may be administered to the subject about 14 hours prior to the colonoscopy. This initial dose may be followed by a second aliquot of the composition administered about 3 hours prior to the colonoscopy. The subject should consume large amounts of liquids, 3 to 4 Liters for example, in addition to the composition to maintain adequate hydration. These additional liquids may include aqueous solutions that include oral re-hydration salts and/or electrolytes, such as GATORADE® and other oral re-hydration beverages.

EXAMPLES

Experimental Plan

A total of 48 male and female Sprague-Dawley rats (150-200 g body weight at start of experiment) were divided in eight groups (A to H) containing 6 animals each (Table 1). On day 1 of the experiment groups A, B, E and F got 30 minutes of bilateral renal ischemia reperfusion injury, while control groups C, D, G and H were sham operated (12) (Table 1). The rats were given 48 hours to recover and BUN and serum creatinine levels were then determined.

On day 3 all groups (A to H) were put on a high phosphorus diet (NIH-07 diet, see reference #6) for 60 days. All groups were dehydrated for 8 hours once a week. While groups B, D, F and H received citrate (2% wt) in their drinking water, the other groups had access to regular tap water, except during periods of dehydration. As rats typically consume a daily average of 10 ml of water per 100 g of body weight, each rat of groups B, D, F and H received an approximate daily dosage of 2 g of citrate per kg of body weight. Literature review (13) indicates that 8 hours of dehydration are sufficient to induce significant changes in distal tubular and interstitial water, electrolyte and osmolyte concentrations in Sprague-Dawley rats.

On day 30 arterial blood samples were collected for pH, BUN and serum creatinine measurements.

On day 60 all animals were sacrificed. Arterial blood samples were collected for serum pH, phosphorus, BUN and creatinine measurements. Bladder urine samples were collected for pH measurements. Kidneys were longitudinally dissected, formalin fixed and paraffin embedded for generation of light microscopic sections. Additional paraffin embedded tissue sections were stained with "von Kossa" stain for calcium crystal identification and LM tissue sections were scored for acute tubular injury as described elsewhere [14].

TABLE 1

| GROUP | A | B | C | D | E | F | G | H |
|---|---|---|---|---|---|---|---|---|
| GENDER | M | M | M | M | F | F | F | F |
| SURGERY | I/R | I/R | Sh | Sh | I/R | I/R | Sh | Sh |
| TREATMENT | $H_2O$ | Citrate | $H_2O$ | Citrate | $H_2O$ | Citrate | $H_2O$ | Citrate |
| DIET | HP | HP | HP | HP | HP | HP | HP | HP |
| DURATION | 60 d | 60 d | 60 d | 60 d | 60 d | 60 d | 60 d | 60 d |

M = male;
F = female;
I/R = ischemia/reperfusion;
Sh = sham operated;
HP = high phosphate;
d = days.

Statistically significant differences between experimental groups were determined using Bonferroni t-tests and analysis of variance.

Figure 1:
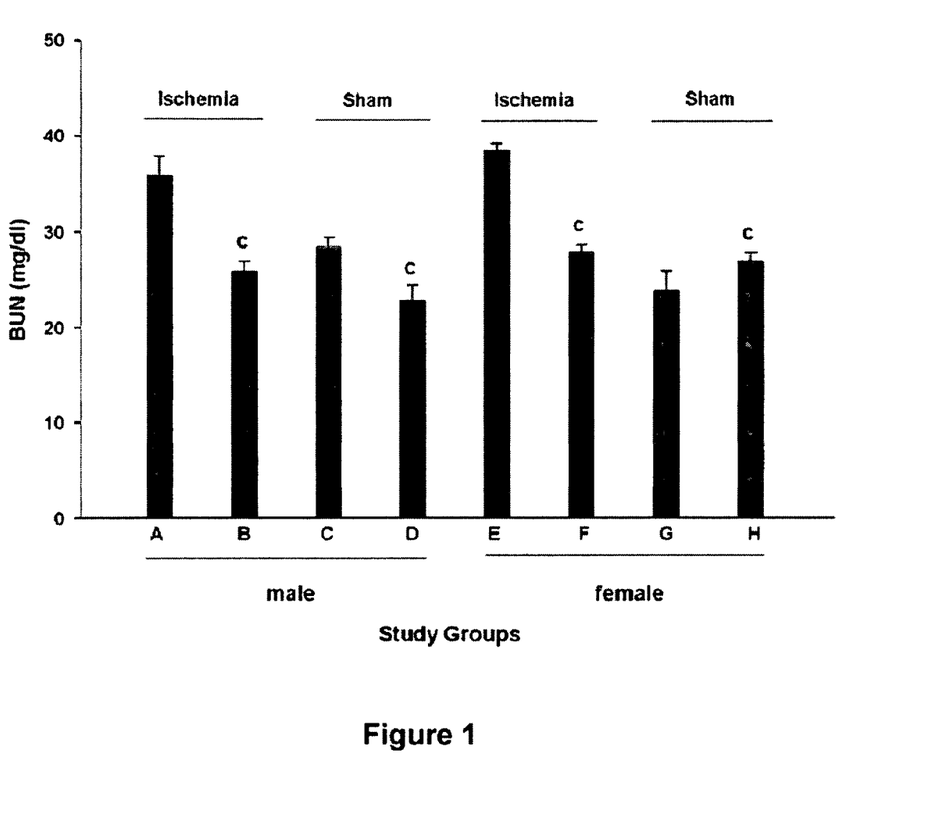
FIG. 1 illustrates serum BUN levels in male and female rats with or without I/R or citrate at day 60 of the experiment.

Results:

Effect of citrate on renal function and serum phosphorus levels: Serum BUN levels in female rats with I/R injury had increased by 40% after 60 days of high phosphate diet and dehydration without citrate, compared to their controls (E vs. G, FIG. 1). BUN levels in male rats with I/R had increased by 20% compared to controls (A vs. C, FIG. 1). Addition of citrate (2% wt) in drinking water markedly ameliorated renal function decline in both male and female animals with I/R and returned BUN levels to near control values (B & F, FIG. 1).

Figure 2:
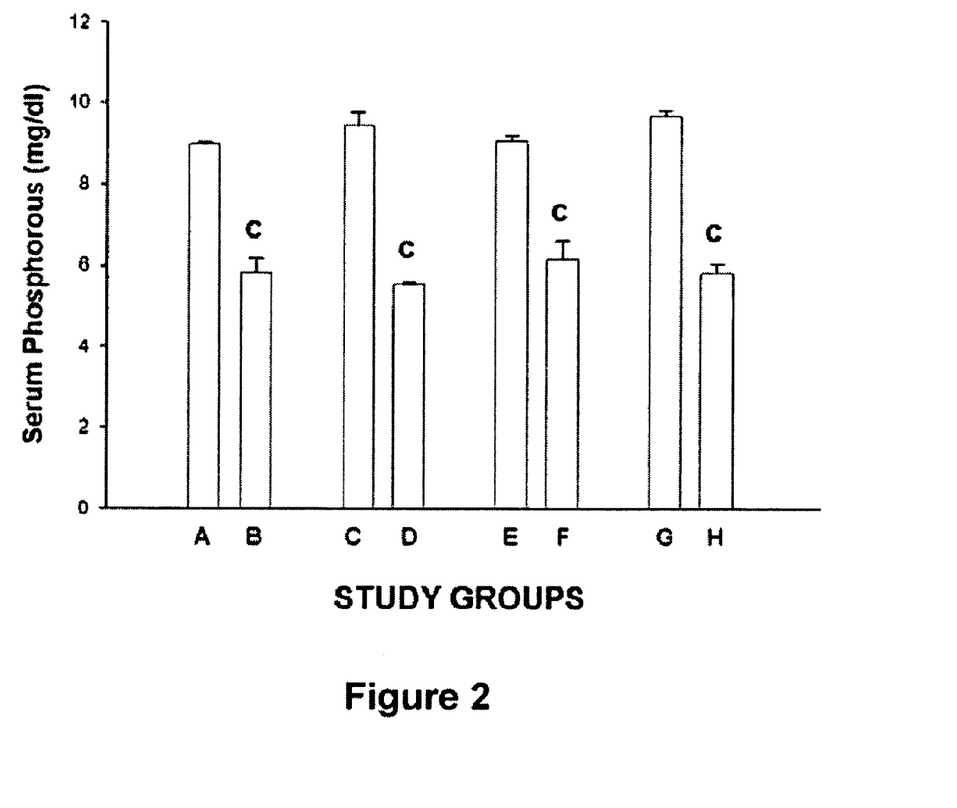
FIG. 2 illustrates serum phosphorous levels in the rat study groups of FIG. 1, at day 60 of the experiment.
Figure 3:
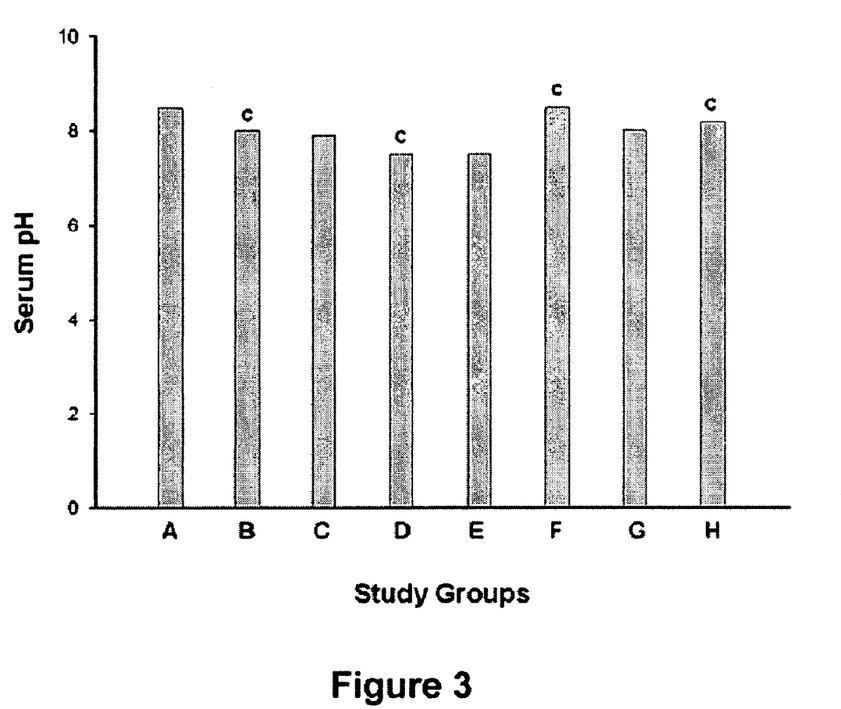
FIG. 3 illustrates the serum pH in all study groups at day 60.
Figure 4:
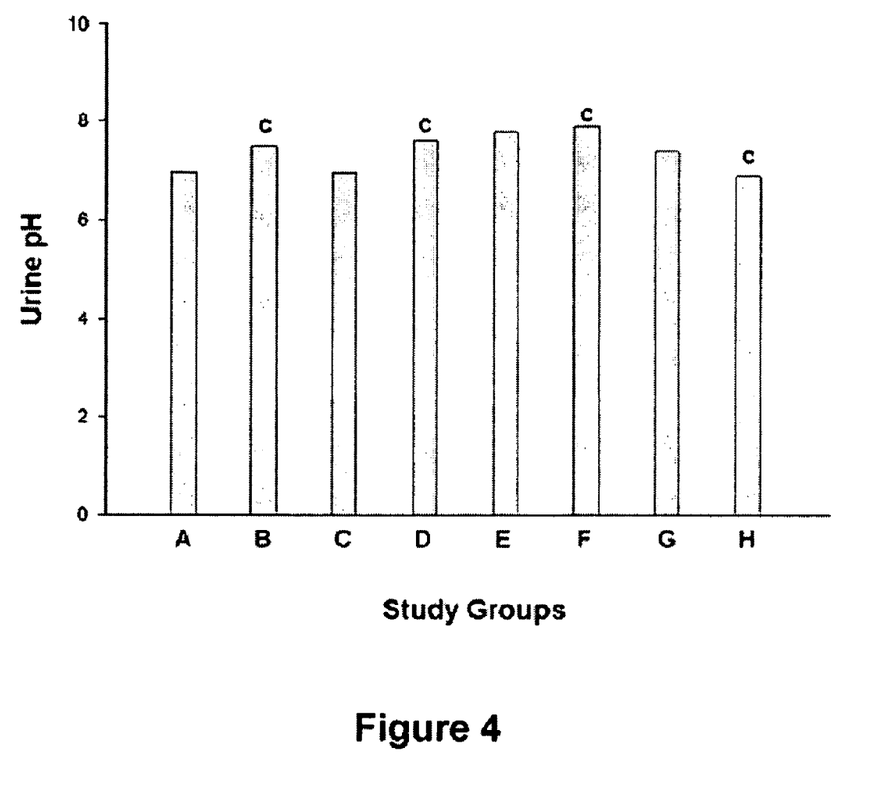
FIG. 4 illustrates the urine pH in all study groups at day 60.

Both male and female groups with I/R or sham operation, without citrate in drinking water, showed markedly elevated serum phosphorus levels due to a high phosphate diet. In these animals serum phosphorus levels were increased up to three times normal (FIG. 2). Addition of citrate to drinking water decreased serum phosphorus levels by 30% in all groups (FIG. 2; citrate-treated groups are denoted with the letter "C"). Citrate did not have a significant effect on either serum or urine pH values (FIGS. 3 and 4).

Figure 5:
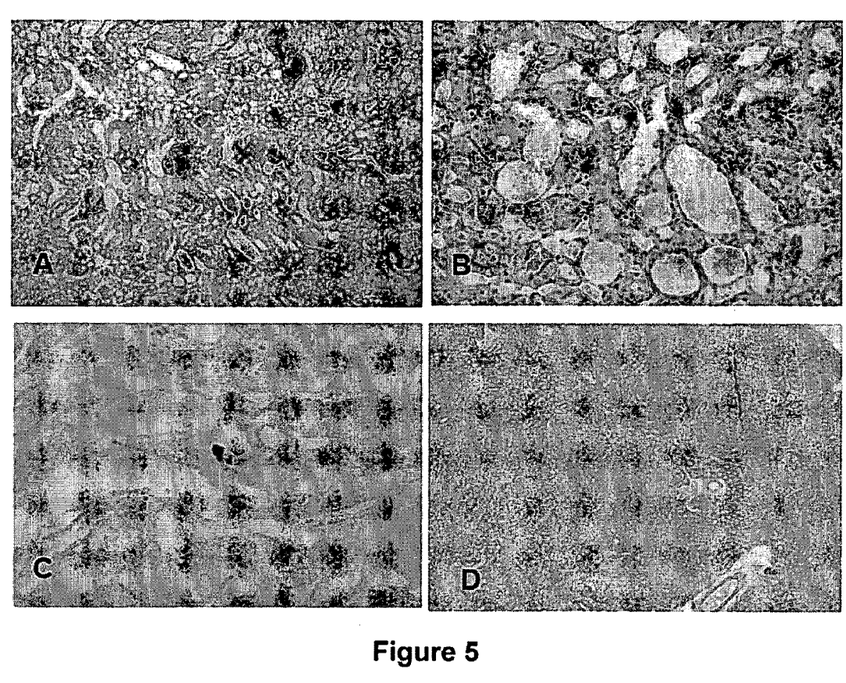
FIG. 5 illustrates histological sections of the kidneys of male rats subjected to I/R injury.

Histological evaluation of acute tubular injury and calcium phosphate crystal formation: Male rats with I/R injury but without citrate supplementation showed extensive tubular dilation with multiple intraluminal casts (Tamm-Horsfall casts) (FIG. 5A), flattening of epithelial cells with regenerative changes and sloughing of injured cells, consistent with acute tubular necrosis. Higher power showed dilated tubules with flattened epitheliums (FIG. 5B). Many injured tubules in outer medulla showed periodic acid-Schiff (PAS) positive casts and there were rare occasional calcium crystal deposits in medullary tubes (FIG. 5C). In male I/R animals with citrate supplementation the morphologic changes of ATN were markedly reversed (FIG. 5D).

Figure 6:
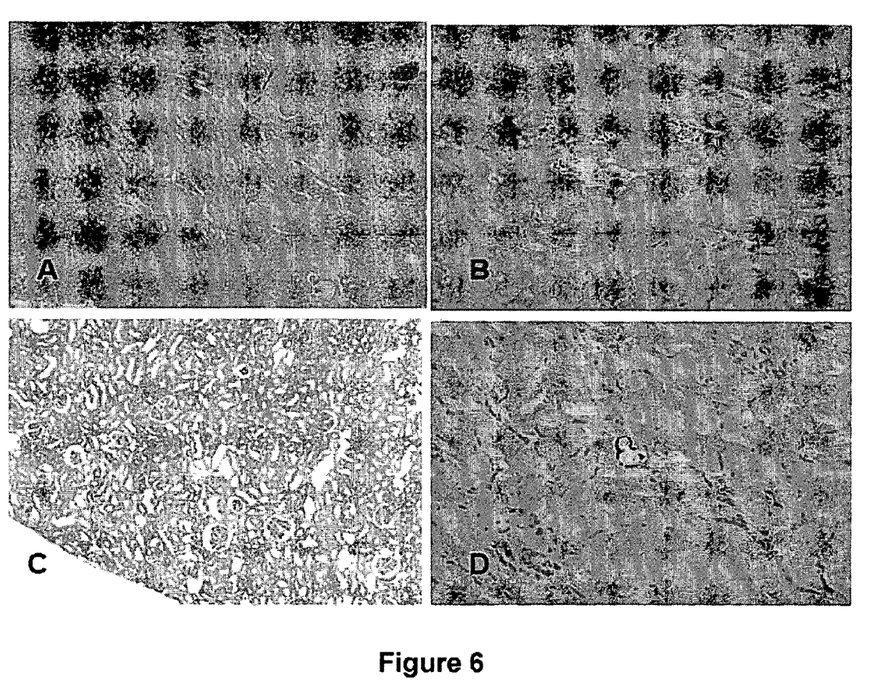
FIG. 6 illustrates histological sections of the kidneys of female rats subjected to I/R injury.

Female rats with I/R injury without citrate showed similar extent and degree of tubular injury as their male counterparts, but a slightly higher number of calcium crystal deposits (FIG. 6). Females subjected to I/R but not to citrate administration exhibited tubular dilation and casts (FIG. 6A). Von Kossa stain showed multiple calcium phosphate crystal deposits in the tubular lumen (FIGS. 6B and 6D). By contrast, female rates with I/R injury but with citrate supplementation exhibited focal tubular dilation but no casts and no calcium phosphate crystals (FIG. 6C).

Figure 7:
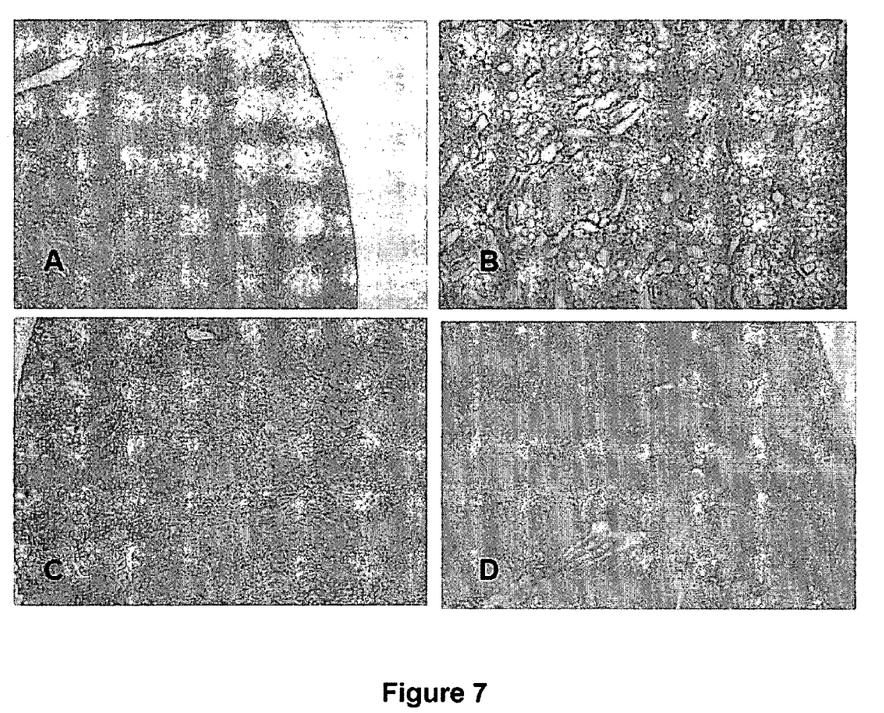
FIG. 7 illustrates histological sections of the kidneys of sham operated rats.

In both male and female sham operated animals, the degree of tubular necrosis was less, although occasional dilated tubules with casts and regenerating epithelium were seen (FIG. 7). Female sham operated rats without (FIG. 7A) or with citrate (FIG. 7C) showed no significant difference in tubular morphology. Male sham operated rats showed focal tubular injury with casts (FIG. 7B) without citrate. Citrate supplementation markedly decreased tubular injury and cast formation (FIG. 7D).

Overall, the experiment showed that phosphate nephropathy is a pathologic entity that may be due to phosphate-induced toxicity to certain cells of the nephron. Gender does not appear to affect the incidence of ATN or the impairment of renal function. Citrate was shown to protect against phosphate nephropathy in specimens on a high phosphate diet and decrease serum phosphorus levels in all study groups. Citrate did not affect serum (FIG. 3) or urine pH (FIG. 4). Without being bound by any particular theory, it appears that citrate has a protective effect because it forms a complex with calcium phosphate.

REFERENCES (1) Isenring, P. et al: NEJM 349: 1006, 2003.
(2) Orias, M. et al: Am J Nephrol 19: 60, 1999.
(3) Markowitz, G. et al: Human Pathology 35: 675, 2004.
(4) Markowitz, G. et al: JASN 16:3389-3396, 2005.
(5) Fine, A. et al: Am J Kid Dis 29: 103, 1997.
(6) Ritskes-Hoitinga, J. et al: J. Nutr. 119: 1423, 1989.
(7) Rao, G. N.: Toxicol Pathol 30: 651, 2002.

(8) Oikawa, T. et al: Kidney Int. 51: 164, 1997.
(9) Ma, L. J. et al: Kidney Int. 64: 350, 2003.
(10) Moeckel, G. W. et al: Am. J. Physiol. 272: F94-F99, 1997.
(11) Moeckel, G. W. et al: JBC 278: 19352, 2003.
(12) Smoyer, W. E. et al: JASN 11:211-221, 2000.
(13) Neuhofer, W. et al: Kidney Int. 65: 431, 2004.
(14) Moeckel, G. W. et al: Am J Physiol. 290: F223-31, 2006.
(15) Marangella, M. et al: Urologia Int., 72:6-10, 2004.
(16) Toblli, J. E. et al: Clin Nephrol 55:59-68, 2001.
(17) Lacour, B. et al: Gastroenterol Clin Biol 18(11):938-944, 1994.
(18) Vanner, S. J. et al: Am. J. Gastroenterol. 85(4): 422-427, 1990.
(19) Vanner, S. J. et al: U.S. Pat. Appl. Publ., Publ. No. US2004/0192614.
(20) Ayala, et al., U.S. Pat. Appl. Publ., Publ. No. US2006/0051428.
(21) U.S. Pat. Appl. Publ., Publ. No. US2004-0071779 A1

What is claimed is:

1. A method of reducing phosphate nephropathy in a mammal suffering from impairment of renal function, comprising: administering to the mammal an amount of citrate effective to reduce serum phosphorous concentration, wherein the amount of citrate is 5 g to 100 g of citrate, and the citrate is selected from the group consisting of citric acid, sodium hydrogen citrate, sodium dihydrogen citrate, citrate esters and mixtures thereof.

2. The method of claim 1, wherein the mammal has ischemia-induced renal failure.

3. The method of claim 1, wherein the mammal has ischemic tubular injury.

4. The method of claim 1, wherein the administering comprises administering orally a solution comprising citrate.

5. The method of claim 1, wherein the administering comprises administering intravenously a solution comprising citrate.

6. The method of claim 1, wherein the administering comprises administering orally a solid composition comprising citrate.

7. The method of claim 1, wherein the administering comprises administering during dialysis.

8. The method of claim 1, wherein the administering comprises administering from 10 g to 50 g of citrate.

* * * * *

UNITED STATES PATENT AND TRADEMARK OFFICE
CERTIFICATE OF CORRECTION

| | | |
|---|---|---|
| PATENT NO. | : 8,129,430 B2 | Page 1 of 1 |
| APPLICATION NO. | : 12/195853 | |
| DATED | : March 6, 2012 | |
| INVENTOR(S) | : Michael L. Caswell and Gilbert W. Moeckel | |

It is certified that error appears in the above-identified patent and that said Letters Patent is hereby corrected as shown below:

On the title page, item [73] please insert: --Vanderbilt University, Nashville, TN (US)-- after "Assignee: C.B. Fleet Company, Inc., Lynchburgh, VA (US)"

Signed and Sealed this
Twenty-ninth Day of October, 2013

Teresa Stanek Rea
*Deputy Director of the United States Patent and Trademark Office*